(12) United States Patent
Komuro

(10) Patent No.: US 12,121,314 B2
(45) Date of Patent: Oct. 22, 2024

(54) MANIPULATOR SYSTEM, AND CONTROL METHOD OF MANIPULATOR SYSTEM

(71) Applicant: OLYMPUS CORPORATION, Tokyo (JP)

(72) Inventor: Takahiro Komuro, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 749 days.

(21) Appl. No.: 17/191,814

(22) Filed: Mar. 4, 2021

(65) Prior Publication Data

US 2021/0186306 A1 Jun. 24, 2021

Related U.S. Application Data

(63) Continuation of application No. PCT/JP2018/033220, filed on Sep. 7, 2018.

(51) Int. Cl.
*A61B 34/00* (2016.01)
*A61B 1/00* (2006.01)
*A61B 1/005* (2006.01)

(52) U.S. Cl.
CPC .......... *A61B 34/70* (2016.02); *A61B 1/00042* (2022.02); *A61B 1/0052* (2013.01); *A61B 1/0057* (2013.01); *A61B 34/74* (2016.02)

(58) Field of Classification Search
CPC ..... A61B 34/70; A61B 1/0052; A61B 1/0057; A61B 34/74; A61B 1/00006; A61B 34/71; A61B 34/30; A61B 2090/066
See application file for complete search history.

(56) References Cited

U.S. PATENT DOCUMENTS

2007/0015967 A1\* 1/2007 Boulais .............. A61B 1/00147
600/152
2010/0069719 A1\* 3/2010 Wehrheim ......... G02B 23/2476
600/152
(Continued)

FOREIGN PATENT DOCUMENTS

EP 3106077 A1 12/2016
JP H06-189897 A 7/1994
(Continued)

OTHER PUBLICATIONS

International Search Report dated Dec. 4, 2018 issued in PCT/JP2018/033220.

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

A manipulator system, has an elongated portion having a bending portion and a wire configured to bend the bending portion; an operation portion configured to generate a first force for pulling the wire by an operator; a motor configured to generate a second force for pulling the wire; a clutch mechanism configured to switch a pulling force to pull the wire between to at least one of the first force or the second force; a grasping-state detector configured to determine a grasping state of the operation portion by the operator; and a controller configured to control the motor and the clutch mechanism, wherein the controller is configured to obtain the grasping state from the grasping-state detector, generate a control signal for controlling the clutch mechanism according to the obtained grasping state, and transmit the control signal to the clutch mechanism.

11 Claims, 9 Drawing Sheets

(56) References Cited

U.S. PATENT DOCUMENTS

| | | | |
|---|---|---|---|
| 2011/0263983 A1* | 10/2011 | Peszynski | A61B 8/445 600/443 |
| 2015/0080658 A1* | 3/2015 | Chung | A61B 1/00042 600/152 |
| 2015/0100066 A1* | 4/2015 | Kostrzewski | A61B 34/30 606/130 |
| 2018/0098687 A1* | 4/2018 | Sholev | A61B 1/045 |
| 2018/0228557 A1* | 8/2018 | Darisse | A61B 1/0057 |
| 2019/0231449 A1* | 8/2019 | Diolaiti | A61B 1/0016 |
| 2020/0188046 A1* | 6/2020 | Overmyer | A61B 34/20 |
| 2020/0253678 A1* | 8/2020 | Hulford | A61B 34/25 |
| 2021/0128260 A1* | 5/2021 | Gonenc | A61B 17/3423 |
| 2023/0148848 A1* | 5/2023 | Gono | A61B 1/00006 600/104 |

FOREIGN PATENT DOCUMENTS

| | | |
|---|---|---|
| JP | 2003-265402 A | 9/2003 |
| JP | 2015-188504 A | 11/2015 |
| WO | WO 2015/122283 A1 | 8/2015 |

\* cited by examiner

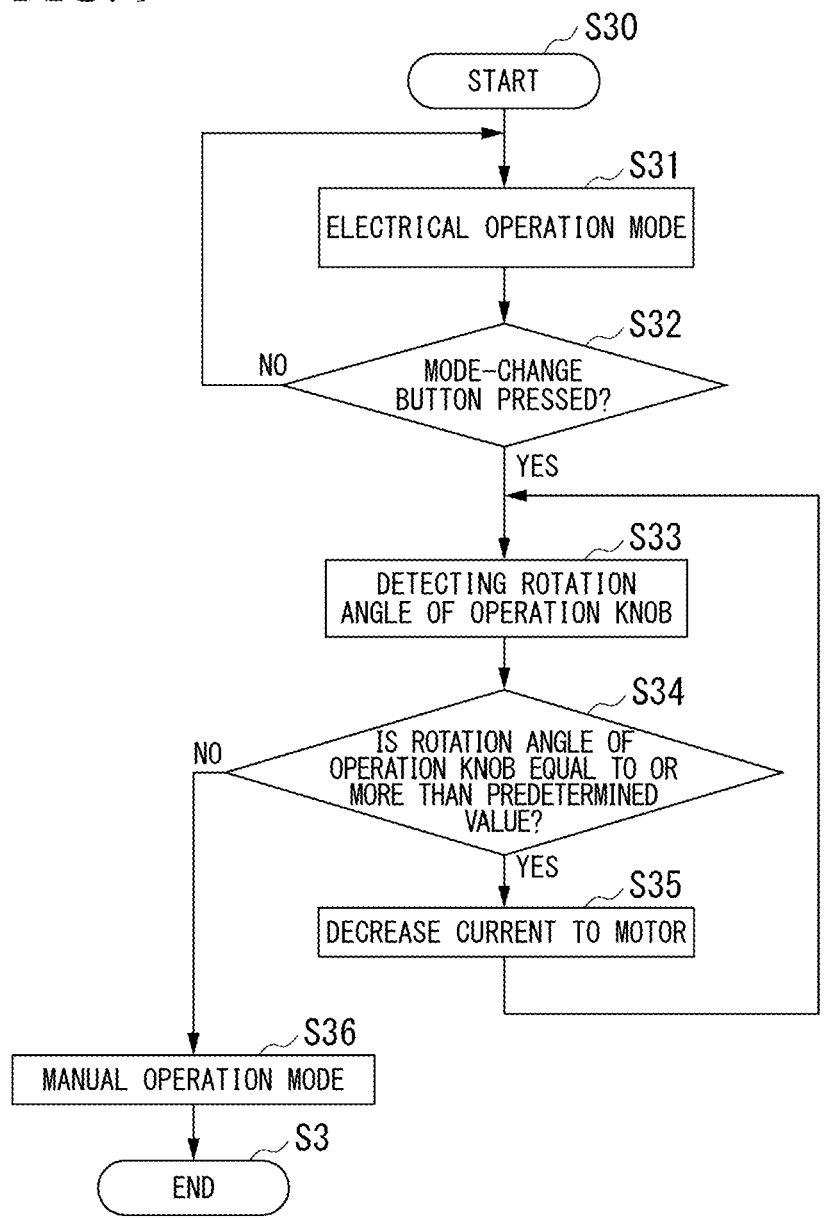

MANIPULATOR SYSTEM, AND CONTROL METHOD OF MANIPULATOR SYSTEM

This application is a continuation application based on a PCT International Application No. PCT/JP2018/033220, filed on Sep. 7, 2018. The content of the PCT International Application is incorporated herein by reference.

TECHNICAL FIELD

The present disclosure relates to a manipulator system such as an endoscope system, and a control method of a manipulator system.

BACKGROUND ART

Conventionally, a manipulator system such as an endoscope system and the like, wherein an operation of a bending portion of the endoscope may be switched between an electrical operation and a manual operation, is utilized. According to such a manipulator system, it is possible to perform an automatic operation of the bending portion of the endoscope by the electrical operation and an electrical assistance and the like by the manual operation of an operator.

An endoscope apparatus having a clutch mechanism configured to switch the operation of the bending portion between the electrical operation and the manual operation is disclosed in Japanese Unexamined Patent Application, First Publication No. H6-189897. According to the endoscope apparatus disclosed in Japanese Unexamined Patent Application, First Publication No. H6-189897, when the electrical operation is switched to the manual operation by the clutch mechanism and the transmission of an electrical driving force to the bending portion is canceled, a regulation operation for preventing the bending portion from sharply restoring is temporarily performed if a bending angle of the bending portion is large.

SUMMARY

According to an aspect of the present disclosure, a manipulator system has an elongated portion having a bending portion and a wire configured to bend the bending portion; an operation portion configured to generate a first force for pulling the wire by an operator; a motor configured to generate a second force for pulling the wire; a clutch mechanism configured to switch a pulling force to pull the wire to at least one of the first force or the second force; a grasping-state detector configured to determine a grasping state of the operation portion by the operator; and a controller configured to control the motor and the clutch mechanism, wherein the controller is configured to obtain the grasping state from the grasping-state detector, generate a control signal for controlling the clutch mechanism according to the obtained grasping state, and transmit the control signal to the clutch mechanism.

According to another aspect of the present disclosure, a manipulator system has an elongated portion having a bending portion and a wire configured to bend the bending portion; an operation portion configured to generate a first force for pulling the wire by an operator; a motor configured to generate a second force for pulling the wire; a switching mechanism configured to switch a pulling force to pull the wire between at least one of the first force or the second force; and a controller configured to control the motor and the switching mechanism, wherein the controller is configured to determine possibility of switching the second force to the first force, and allow the switching when the switching is determined to be possible.

According to a further aspect of the present disclosure, a method for controlling an endoscope system, wherein the endoscope system is configured to be switchable between a first mode in which an bending portion of an endoscope is bent due to a driving force of a motor and a second mode in which the bending portion of the endoscope is bent by a manual operation of an operation portion, the method includes determining possibility of switching the first mode to the second mode, and allowing the switching when the switching is determined to be possible.

BRIEF DESCRIPTION OF DRAWINGS

FIG. 9 is a flow chart showing the control by the control portion when the operation mode is switched from the electrical operation mode to the manual operation mode in the endoscope system.

DESCRIPTION OF EMBODIMENT

First Embodiment

A first embodiment of the present disclosure will be described with reference from FIG. 1 to FIG. 6.

Figure 1:
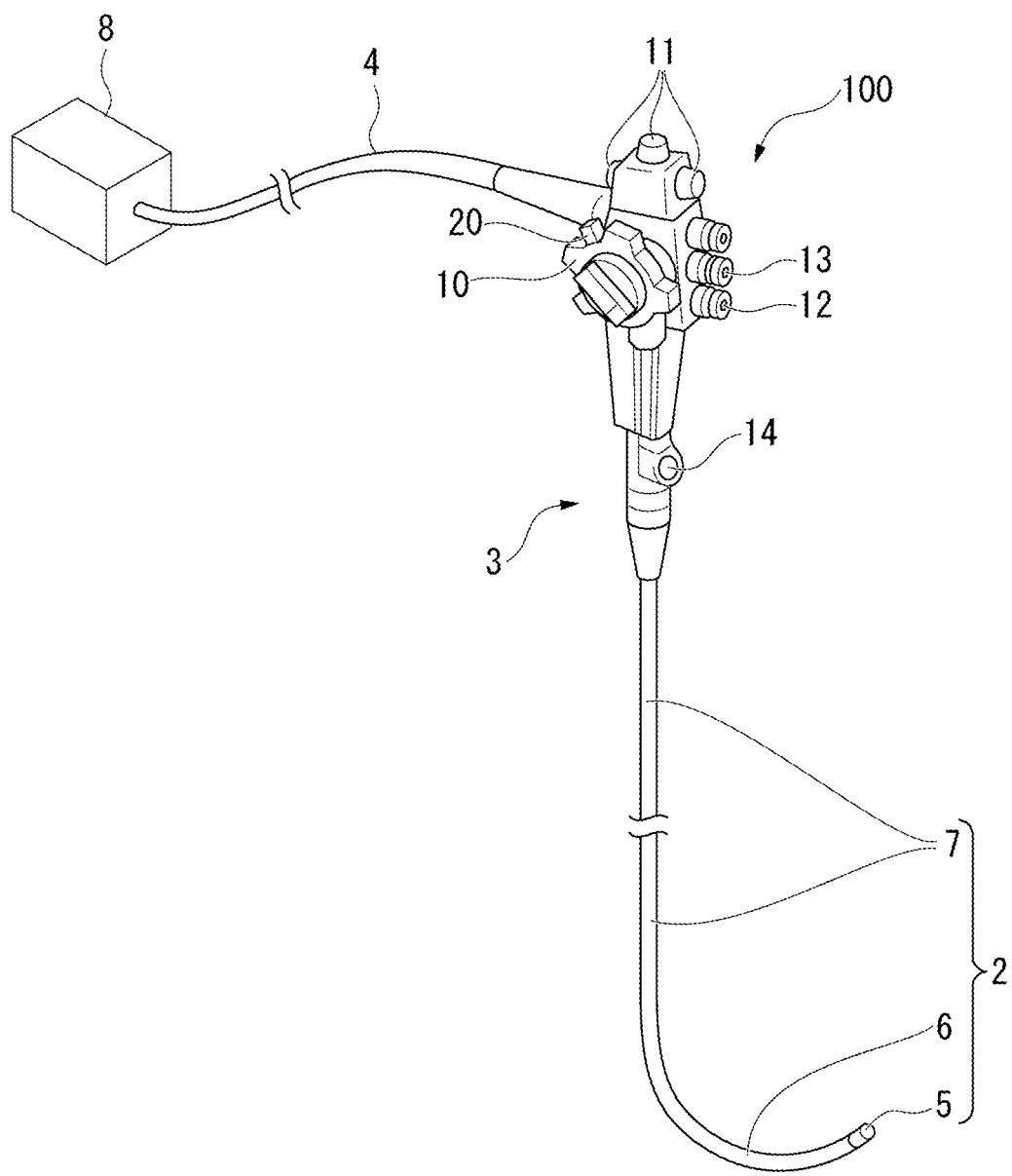
FIG. 1 is a view showing a whole configuration of an endoscope system according to the first embodiment of the present disclosure.

FIG. 1 is a view showing a whole configuration of an endoscope system 100 according to the present embodiment.

As shown in FIG. 1, the endoscope system (manipulator system) 100 has an insertion portion 2, an operation portion 3, a universal cable 4, and a main body 8.

The insertion portion (elongated portion) 2 is an elongated member to be inserted into an observation target site. A distal end portion 5, a bending portion 6, and a flexible tube portion 7 is provided continuously in a sequence from a distal end side of the insertion portion 2.

The distal end portion 5 has an illumination optical system (not shown) having a light guide and an imaging portion having an imaging device (not shown) built in the distal end portion 5. The bending portion 6 is configured to be freely bendable toward an upward direction and a downward direction, or left and right. The flexible tube portion 7 is a tube-shaped member being elongated and flexible.

Figure 2:
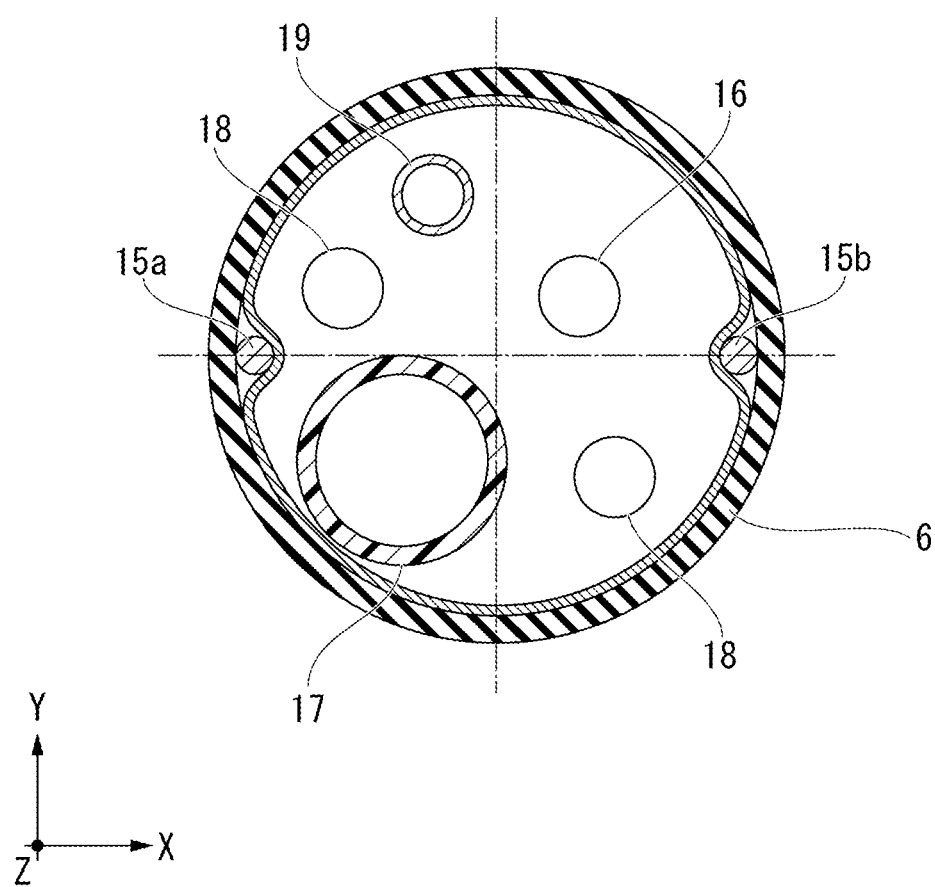
FIG. 2 is a cross-sectional view showing a bending portion of the endoscope system.

FIG. 2 is a cross-sectional view of the bending portion 6.

Two wires 15a, 15b configured to bend the bending portion 6, an imaging cable 16 being connected to the imaging portion, a treatment device channel tube 17, two light guide fiber bundles 18, an air-and-water supply tube 19 and the like are inserted through the bending portion 6 along a longitudinal axis 2a of the insertion portion 2.

The wires 15a, 15b are corresponding to the two bending directions of the upward direction and the downward direction, or left and right. Distal ends of the two wires 15a, 15b are connected to the distal end portion 5. The two wires 15a, 15b are inserted through the distal end portion 5, the bending portion 6, and the flexible tube portion 7 along the longitudinal axis 2a of the insertion portion 2 and extend to the operation portion 3 disposed at a proximal end side of the flexible tube portion 7.

The operation portion 3 has an operation knob (operation input portion) 10, various switches 11, an air-and-water supply button 12, a suction button 13, a treatment device insertion port 14 and the like are provided on an external circumferential portion of the operation portion 3. The various switches 11 refer to operation-mode-switching button 11a and the like. An angle lock configured to lock the operation knob 10 is also disposed in the operation portion 3.

The bending portion 6 may be configured to be freely bendable in four directions, the upward direction, the downward direction, left and right. In this case, four wires 15 are provided corresponding to the bending directions of the upward direction, the downward direction, left and right, and the operation knobs 10 is configured to have a upward-downward bending knob and a left-right bending knob for example.

Figure 3:
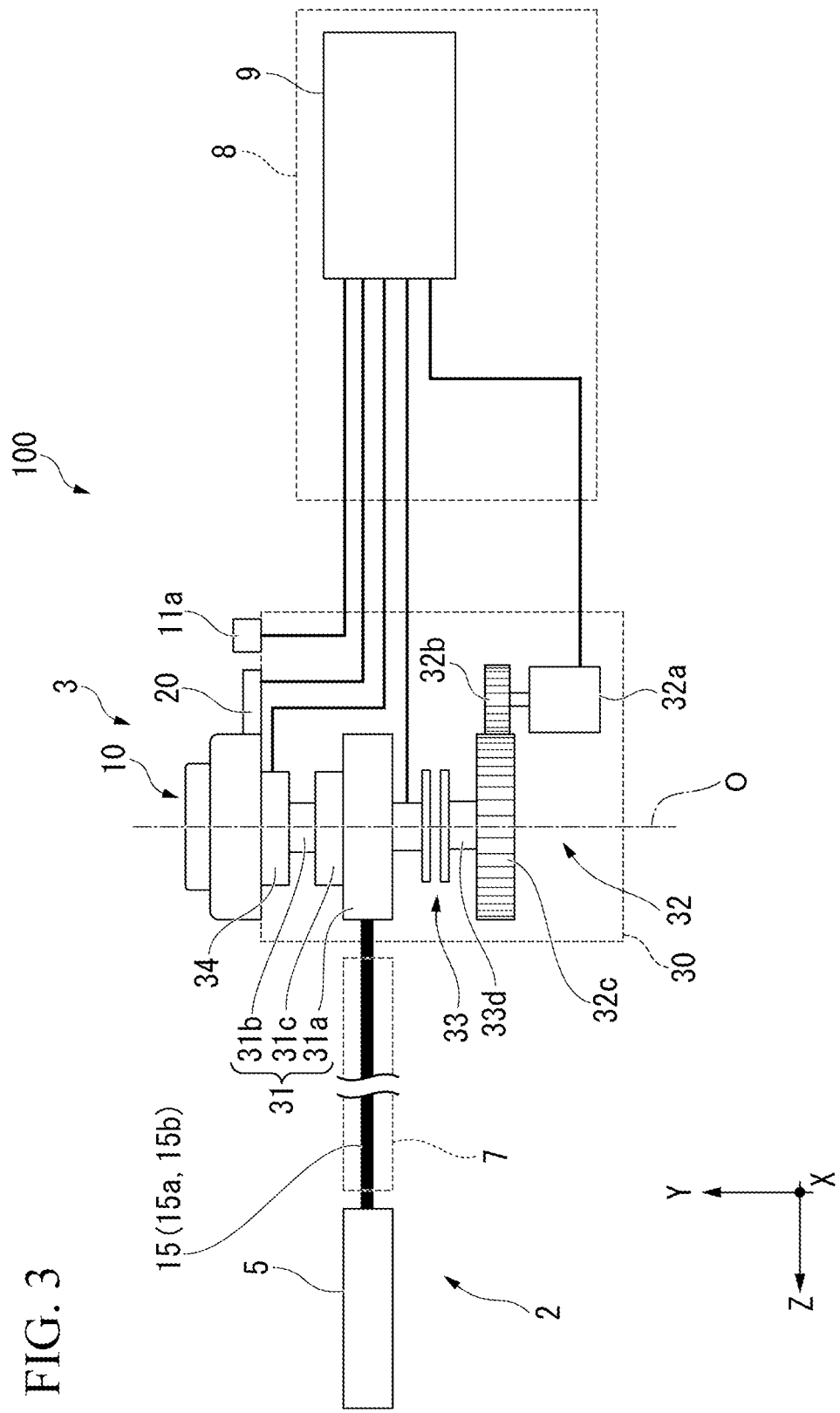
FIG. 3 is a schematic diagram showing an insertion portion, an operation portion, and a controller of the endoscope system.

FIG. 3 is a schematic view showing the insertion portion 2, the operation portion 3 and the main body 8.

The operation portion 3 has a bending operation portion 30 configured to operate the bending portion 6 therein. The bending operation portion 30 has a wire traction portion 31, an electrical driving portion 32, a clutch mechanism 33, and a grasping-detection portion 34.

The wire traction portion 31 is configured to pull the wires 15a, 15b extending from the flexible tube portion 7. The wire traction portion 31 has a traction pulley 31a configured to pull the wires 15a, 15b, a first shaft member 31b supporting the pulley 31a so as to be rotatable, and a potentiometer 31c configured to determine a rotation angle of the pulley 31a.

In the following description, the direction along the longitudinal axis of the insertion portion 2 is referred to a Z-axis direction, the axial direction of the first shaft member 31b is referred to a Y-axis direction, and a direction orthogonal to the Z-axis direction and the Y-axis direction is referred to an X-axis.

The pulley 31a is a disc-shaped member rotating around the first shaft member 31b as a rotation center. When the pulley 31a rotates, the pulley 31a pulls either of the wires 15a, 15b whose proximal ends are attached to the external circumference of the pulley 31a. A wire formed by connecting the proximal ends of the two wires 15a, 15b may be hooked to the external circumference of the pulley 31a. In the following description, a state of the pulley 31a in which distances from the pulley 31a to the proximal ends of the two wires 15a, 15b are the same with each other is defined as an "initial state" of the pulley 31a.

The first shaft member 31b is a rod-shaped member as the rotation center O of the pulley 31a. An end portion of the first shaft member 31b is connected to the operation knob 10. The other end portion of the first shaft member 31b is connected to the clutch mechanism 33 by penetrating the pulley 31a.

The potentiometer 31c is configured to determine the rotation angle of the pulley 31a. The rotation angle of the pulley 31a in the initial state is defined as "zero". The potentiometer 31c may be suitably selected from the well-known potentiometers that can determine angles. The determined rotation angle is output to the main body 8.

The operation knob (operation input portion) 10 is an input portion of a force (first force) for the operator to input a force (first force) to rotate the pulley 31a so as to pull the wires 15a, 15b. The operation knob 10 is connected to the first shaft member 31b, and the first force is transmitted to the pulley 31a via the first shaft member 31b. The operator may rotate the first shaft member 31b and the pulley 31a by rotating the operation knob 10 around the Z-axis as the rotation center.

The operation knob (operation input portion) 10 is biased such that the pulley 31a returns to the initial position if there is no operation input from the operator. Accordingly, when the operator takes hands off from the operation knob 10, the pulley 31a returns to the initial state and the bending portion 6 enters a "straight state" in which the bending portion 6 is not bent.

The electrical driving portion 32 is configured to generate a force (second force) for rotating the pulley 31a so as to pull the wires 15a, 15b by the electric power. The electrical driving portion 32 has a motor 32a, a first gear 32b connected to a rotation shaft of the motor 32a, a second gear 32c engaged with the first gear 32b, and a second shaft member 32d being the rotation axis of the second gear 32c. The second shaft member 32d is connected to the clutch mechanism 33.

The clutch mechanism 33 has a clutch configured to switch whether to transmit the second force to the first shaft member 31b. The clutch mechanism 33 is configured to switch whether to connect the first shaft member 31b and the second shaft member 32d. The switching by the clutch mechanism 33 may be an electromagnetic type or a mechanical type.

In a case in which the connection between the first shaft member 31b and the second shaft member 32d is canceled (the case in which the clutch is disengaged), the second force cannot be transmitted to the first shaft member 31b. The first shaft member 31b is rotated only by the first force. In other words, the wires 15a, 15b are pulled only by the manual operation of the operator. This operation mode is defined as a "manual operation mode".

In a case in which the connection between the first shaft member 31b and the second shaft member 32d is maintained (the case in which the clutch is engaged), the second force can be transmitted to the first shaft member 31b. The first shaft member 31b is rotated by the second force. That is, the wires 15a, 15b are pulled due to the electrical operation of the electrical driving portion 32. This operation mode is defined as an "electrical operation mode". The first shaft member 31b and the operation knob 10 are still connected such that when the first shaft member 31b is rotated by the second force, the operation knob 10 also rotates.

The switching of the clutch of the clutch mechanism 33 and the driving of the motor 32a of the electrical driving portion 32 are controlled by the main body 8 according to operations modes such as the manual operation mode and the electrical operation mode.

The grasping-detection portion 34 is configured to detect the grasping state when the operation knob is grasped by the hand of the operator. The grasping-detection portion 34 may be suitably selected from the well-known three-axis torque sensors. The grasping-detection portion 34 is configured to detect the rotation torque around the Z-axis as the rotation center that is input by the operator to the operation knob 10. The grasping-detection portion 34 may detect the force in the Z-axis direction that is input by the operator to the operation knob 10. The detected grasping state is output to the main body 8.

The universal cable 4 extends from the lateral portion of the operation portion 3. An end of the universal cable 4 is connected to the main body 8.

The main body 8 has a control portion 9 configured to control the bending operation portion 30 of the operation portion 3.

Figure 4:
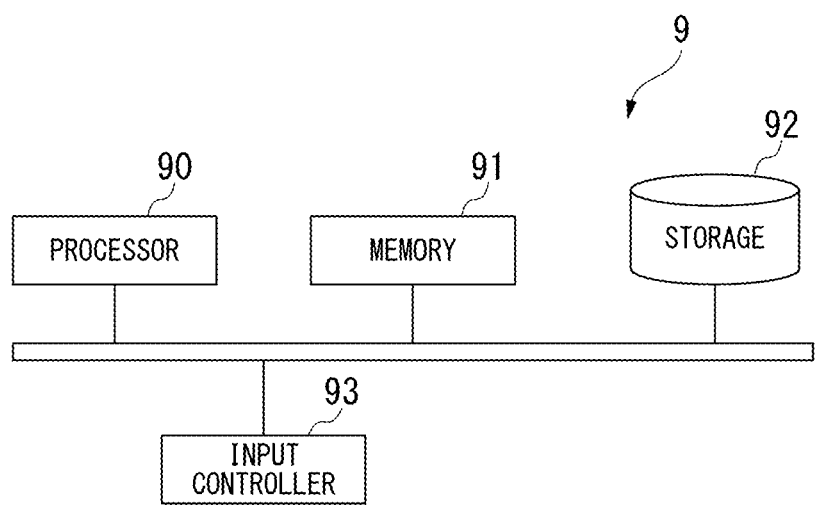
FIG. 4 is a view showing a configuration a control portion of the endoscope system.

FIG. 4 is a configuration view of the control portion 9. The control portion 9 is a processing device (computer) capable of executing program and having a processor 90, a memory 91 capable of reading program, a storage 92 capable of storing program and data, and an input-output control portion 93. The functions of the control portion 9 are realized by the processor executing the program supplied to the control portion 9.

The processor 90 may obtain the input states of the buttons such as the angle lock 20, the operation-mode-switching buttons 11a and the like that are provided in the operation portion 3 via the input-output control portion 93. The processor 90 obtains the grasping state detected by the grasping-detection portion 34 via the input-output control portion 93. The processor 90 may control the electrical-driving portion 32 and the clutch mechanism 33 via the input-output control portion 93.

The program by be provided by the "computer-readable recording medium" such as a CD-ROM, a flash memory and the like. The program may be transmitted from the computer having the storage where the program is stored to the endoscope system 100 through the transmission medium or transmission wave in the transmission medium. The "transmission medium" transmitting the program refers to the medium having the information transmission function such as the internet and the like among the networks (communication network) and the telephone line and the like among the communication circuit (communication lines). Furthermore, the program may be a differential file (differential program) which is combined with the program already recorded in the control portion 9 so as to realize the functions of the control portion 9.

The main body 8 has a display portion that is not shown in figures. The display portion is a LED, a display panel and the like. The display portion may display warning messages and the like to the operator by the control of the control portion 9.

The operations of the endoscope system 100 having the above-described configurations will be described by referring to the flow chart shown in FIG. 5 and FIG. 6.

[Switching Operation from Electrical Operation Mode to Manual Operation Mode]

Figure 5:
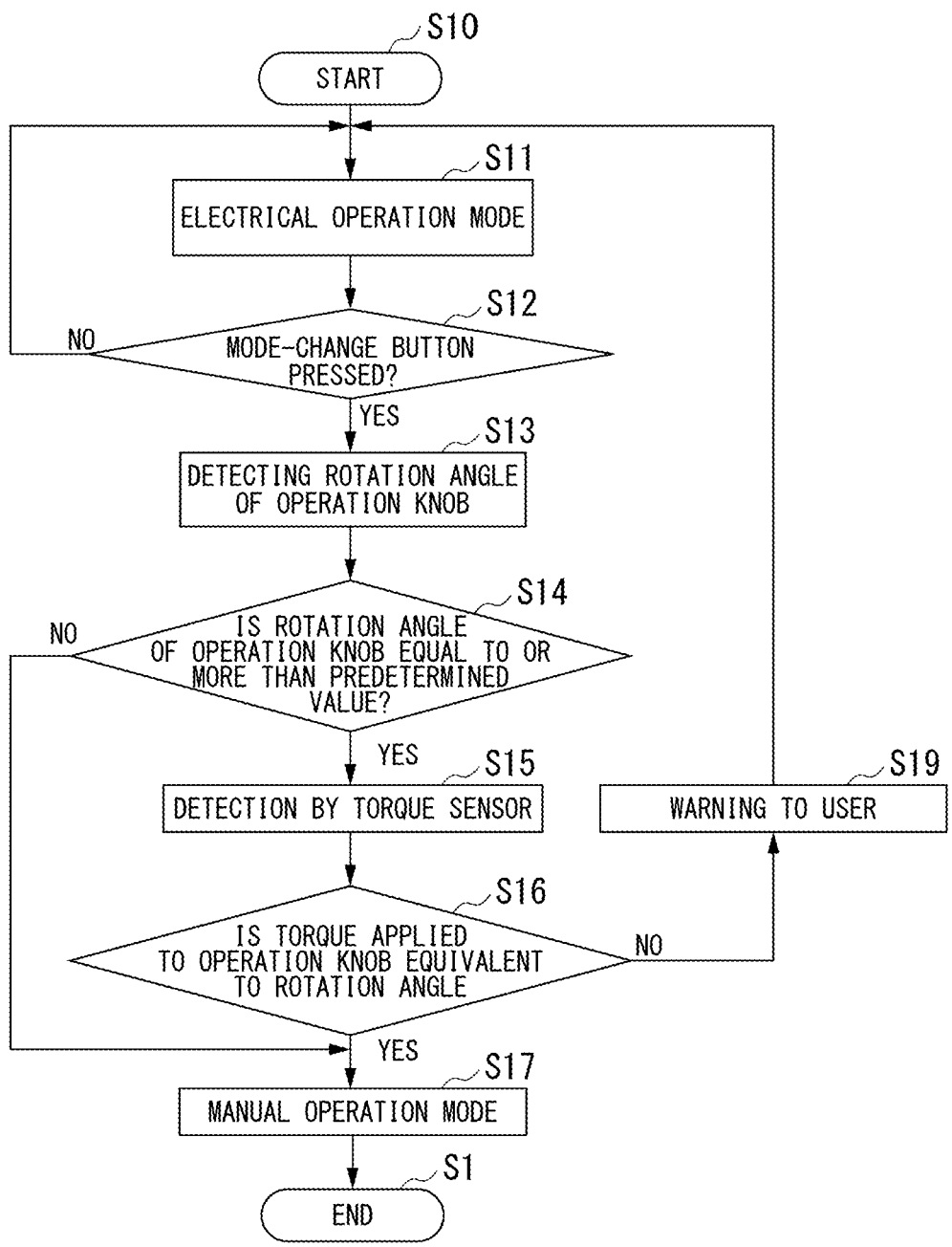
FIG. 5 is a flow chart showing the control by the control portion when an operation mode is switched from an electrical operation to a manual operation in the endoscope system.

FIG. 5 is a flow chart regarding the control of the control portion 9 when the operation mode is switched from the electrical operation mode to the manual operation mode. As shown in FIG. 5, when the operation mode of the control portion 9 is switched to the electrical operation mode, the control portion 9 starts the control of the electrical operation mode (Step S10). Next, the control portion 9 executes Step S11.

During Step S11, in a case in which the operation mode is not the electrical operation mode, the control portion 9 controls the clutch mechanism 33 so as to connect the first shaft member 31b and the second shaft member 32d (engage the clutch). The control portion 9 drives the motor 32a of the electrical driving portion 32 to electrically control the bending portion 6. After a predetermined period, the control portion 9 subsequently executes Step S12.

During Step S12, the control portion 9 detects whether the operation-mode-switching button 11a is pressed. In a case in which it is detected that the operation-mode-switching button 11a is pressed, it is intended that the operator changes the operation mode from the electrical operation mode to the manual operation mode. In this case, the control portion subsequently executes Step S13. On the other hand, in a case in which it is not detected that the operation-mode-switching button 11a is pressed, the control portion repeatedly executes Step S11 subsequently.

During Step S13, the control portion 9 obtains the rotation angles of the pulley 31a and the operation knob 10 from the potentiometer 31c. The control portion 9 may accurately obtain the rotation angles of the pulley 31a and the operation knob 10 by the electrical operation. The control portion 9 subsequently executes Step S14.

During Step S14, the control portion 9 determines whether the rotation angle of the operation knob 10 detected in Step S13 is equal to or larger than a predetermined value (for example, 90 degrees). In other words, the control portion 9 determines whether the second force for rotating the operation knob 10 is equal to or larger than the predetermined value. In a case in which the rotation angle is equal to or larger than the predetermined value, the control portion subsequently executes Step S15. In a case in which the rotation angle is not equal to or larger than the predetermined value, even if the clutch of the clutch mechanism 33 is disengaged to cancel the transmission of the second force, the control portion 9 determines that the bending portion 6 does not operate to rapidly approach the straight stage immediately after the disengagement of the clutch. In this case, the control portion 9 subsequently performs Step S17 so as to switch the operation mode to the manual operation mode.

During Step S15, the control portion 9 obtains the rotation torque as part of the grasping state output from the grasping-detection portion 34. Subsequently, the control portion executes Step S16.

During Step S16, the control portion 9 determines whether the rotation torque input to the operation knob 10 by the operator is equivalent to the rotation angle of the operation knob 10 obtained during Step S13. That is, it is determined whether the magnitude and vector of the first force determined from the grasping state is equivalent to the magnitude and vector of the second force. In a case in which the rotation torque has an amount equivalent to the rotation angle of the operation knob 10, even if the clutch of the clutch mechanism 33 is disengaged to cancel the transmission of the second force, the control portion 9 determines that the bending portion 6 does not rapidly operate to enter the straight stage immediately after the disengagement of the clutch. In this case, the control portion subsequently executes Step S17 to switch the operation mode to the manual operation mode.

On the other hand, in the case in which the rotation torque is not equivalent to the rotation angle of the operation knob 10, in the case when the clutch of the clutch mechanism 33 is disengaged to cancel the transmission of the second force, the control portion 9 determines that the bending portion 6 rapidly operates to enter the straight stage immediately after the disengagement of the clutch. In this case, the control portion 9 does not switch the operation mode to the manual operation mode. The control portion 9 subsequently executes Step S19.

The corresponding relationship between the rotation torque input to the operation knob 10 and the rotation angle of the operation knob 10 may be obtained by calculation according to the design information or be obtained according to the result of the prior experiment.

It is preferable to determine the corresponding relationship between the rotation torque input of the operation knob 10 and the rotation angle of the operation knob 10 by taking the error and the clearance of the knob and the wires into consideration so as to associate them in a certain range.

During Step S19, the control portion 9 controls the display portion to show the message such as "Impossible to switch the operation mode to the manual operation mode". In a case in which the display portion is an LED, the control portion 9 lights up the LED. The control portion 9 subsequently executes Steps S11 again. The operator adjusts the rotation torque input to the operation knob 10 and then presses the operation-mode-switching button 11a so as to make another try to switch the operation mode to the manual operation mode.

During Step S17, the control portion 9 disengages the clutch of the clutch mechanism 33 to switch the operation mode to the manual operation mode and finishes the control processing (Step S1).

According to the control processing of the endoscope system 100 described above, by switching the operation mode from the electrical operation mode to the manual operation mode, it is possible to prevent the bending portion 6 from rapidly operating to enter the straight state.

[Operation in Manual Operation Mode]

Next, the operations of the endoscope system 100 during the manual operation mode will be described.

Figure 6:
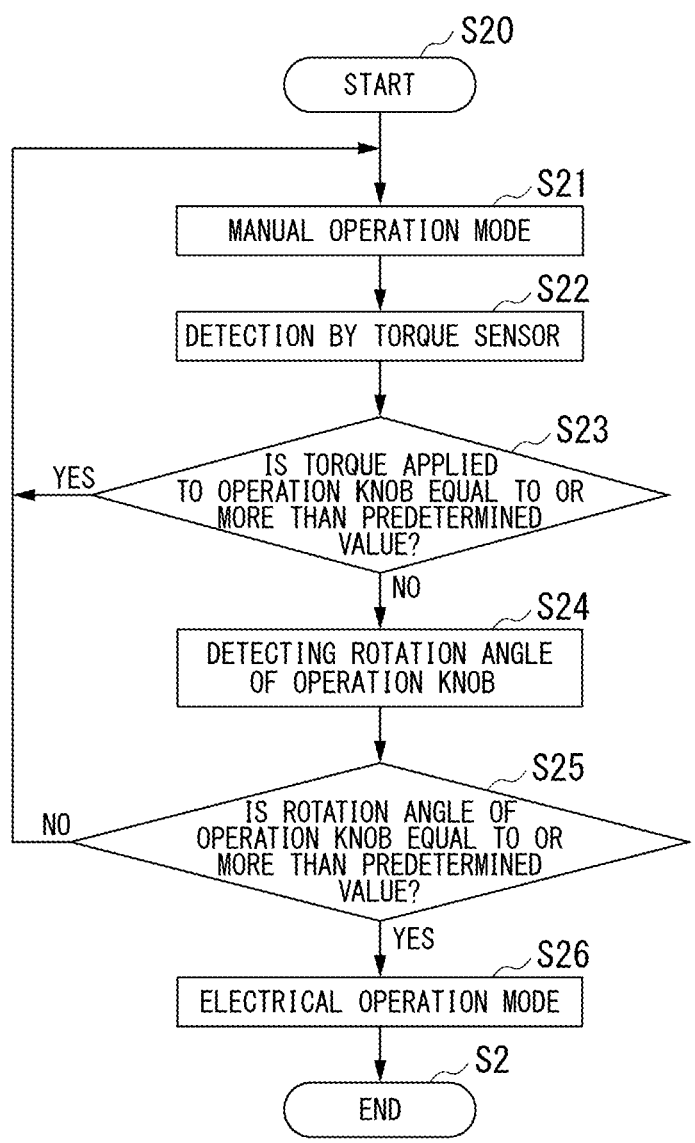
FIG. 6 is a flow chart showing the control of the control portion during the manual operation mode.

FIG. 6 is a flow chart regarding the control of the control portion 9 during the manual operation mode. As shown in FIG. 6, when the operation mode of the control portion 9 is changed to the manual operation mode, the control portion 9 starts the control processing of the manual operation mode (Step S20). The control portion 9 executes Step S21.

During Step S21, in a case in which the operation mode is not the manual operation mode, the control portion 9 controls the clutch mechanism 33 to separate the first shaft member 31b and the second shaft member 32d (disengage the clutch). The operator uses the operation knob 10 to manually control the bending portion 6. After a predetermined period, the control portion 9 subsequently executes Step S22.

During Step S22, the control portion 9 obtains the rotation torque and the force along the Z-axis (hereinafter described as "external force") as part of the grasping state that is output from the grasping-detection portion 34. The control portion 9 subsequently executes Step S23.

During Step S23, the control portion 9 determines whether the external force input to the operation knob 10 by the operator is equal to or larger than the predetermined amount. In the case in which the external force is equal to or larger than the predetermined amount, the control portion 9 determines that the operator is grasping the operation knob 10. In this case, the control portion executes Step S22 again to continue the control in the manual operation mode.

On the other hand, in the case in which the external force input to the operation knob 10 by the operator is not equal to or larger than the predetermined amount, the control portion 9 determines that the operator is not grasping the operation knob 10. In this case, the control portion 9 executes Step S21 again.

During Step S24, the control portion 9 obtains the rotation angle of the pulley 31a and the operation knob 10 from the potentiometer 31c. The control portion 9 may accurately obtain the rotation angle of the pulley 31a and the operation knob 10 being rotated due to the electrical operation. The control portion subsequently executes Step S25.

During Step S25, the control portion 9 determines whether the rotation angle of the operation knob 10 determined during Step S24 is equal to or larger than the predetermined amount (for example, 90 degrees). In the case in which the rotation angle is not equal to or larger than the predetermined amount, even if the operator is not grasping the operation knob 10, the control portion 9 determines that the bending portion 6 does not rapidly operate to approach the straight state. In this case, the control portion 9 executes Step S21 again to continue the control in the manual operation mode.

ON the other hand, in the case in which the rotation angle is equal to or larger than the predetermined amount, since the operator is not grasping the operation knob 10, the control portion 9 determines that the bending portion 6 would rapidly operate to approach the straight state. The control portion 9 subsequently executes Step S26.

During Step S26, the control portion 9 engages the clutch of the clutch mechanism 33 to start the transmission of the second force, then switches the operation mode to the electrical operation mode and finishes the control processing (Step S2). When the operation mode is switched to the transmission operation mode, the control portion 9 drives the motor 32a so as to not to change the rotation angle of the pulley 31a. According to this control, the bending posture of the bending portion 6 is maintained.

According to the control processing of the endoscope system 100 described above, in the case when the operation mode is the manual operation mode, even if the operator takes hands off the operation knob 10, it is possible to prevent the operation that the operation mode is changed to the electrical operation mode and the bending portion 6 rapidly approaches the straight state.

The first embodiment of the present disclosure has been described above in details; however, the specific configuration is not limited to the embodiment, and additions, omissions, substitutions and other changes in the structure are possible without departing from the spirit of the present disclosure. The configuration elements shown in the first embodiment and following modification examples may be suitably combined.

First Modification Example

For example, in the embodiment described above, the embodiment of the manipulator system is not limited to the endoscope system 100 as described above. The manipulator system may be configured to have a robot arm with the treatment device at the distal end thereof while the electrical operation and the manual operation being switched due to the clutch mechanism.

Second Modification Example

For example, in the embodiment described above, it is described that the wire traction portion 31 pulls the wire by the pulley 31a, however, the embodiment of the wire traction portion is not limited thereto. The wire traction portion may pull the wire by a link structure. In this case, the operation input portion may be a lever and the like capable of operating the link structure.

Third Modification Example

For example, in the embodiment described above, it is described that the control portion 9 obtains the rotation angle of the pulley 31a and the operation knob 10 by the potentiometer 31c, however, the embodiment of the configuration for obtaining the rotation angle is not limited thereto. The control portion 9 may obtain the rotation angle by an encoder or the like besides the potentiometer 31c.

Fourth Modification Example

For example, in the embodiment described above, it is disclosed that the control portion 9 detects the grasping state of the operation knob 10 by the three-axis torque sensor, however, the embodiment of the configuration for detecting the grasping state is not limited thereto. The control portion 9 may detect the grasping state by three strain sensors or the like besides the three-axis torque sensor.

Fifth Modification Example

Figure 7:
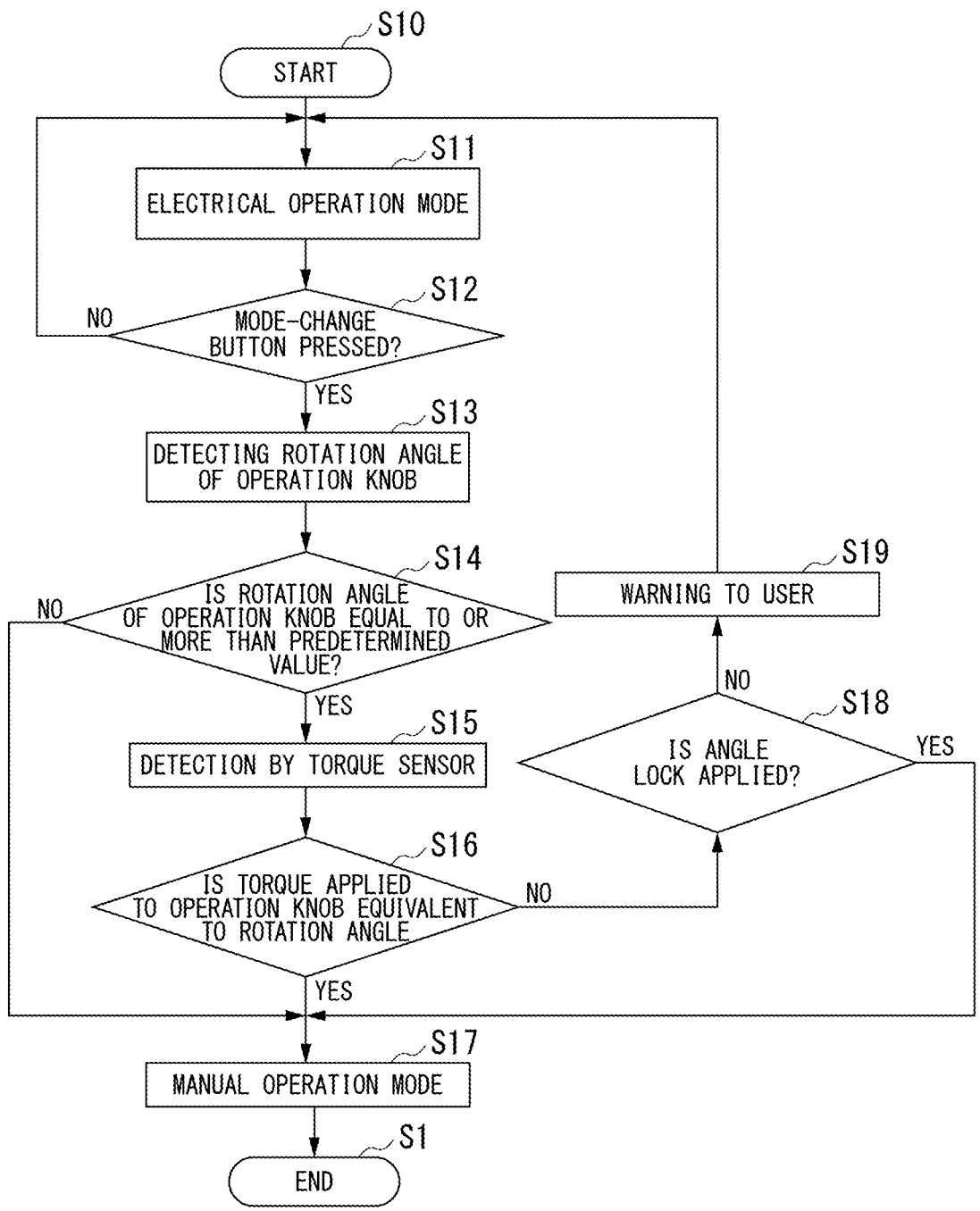
FIG. 7 is a flow chart showing a modification example of the control by the control portion shown in FIG. 5.

For example, in the embodiment described above, it is described that during Step S16, in the case when the rotation torque is not equivalent to the rotation angle of the operation knob 10, the control portion does not switch the operation mode to the manual operation mode. However, the embodiment of switching operation from the electrical operation mode to the manual operation mode by the control portion is not limited thereto. FIG. 7 is a flow chart regarding the control processing of the control portion 9 according to the modification example when the operation mode is switched from the electrical operation mode to the manual operation mode. During Step S16, in the case in which the rotation torque is not equivalent to the rotation angle of the operation knob 10, the control portion 9 subsequently executes Step S18. During Step S18, the control portion 9 detects whether there is a pressing operation to the angle lock 20. In the case in which it is detected that the angle lock 20 is pressed, the pulley 31a is mechanically fixed so as to not to rotate and the wire 15 does not move (angle lock). In this case, even if the clutch of the clutch mechanism 33 is disengaged to cancel the transmission of the second force, the control portion 9 determines that it is necessary to prevent the operation of the bending portion 6 as rapidly approaching the straight state immediately after the cancellation. In this case, the control portion 19 subsequently executes Step S17 so as to switch the operation mode to the manual operation mode.

Second Embodiment

A second embodiment of the present disclosure will be described by referring to FIG. 8 and FIG. 9. In the following description, the common configuration that has been described will be designated with the same reference sign and the duplicated description will be omitted. An endoscope system 100 according to the second embodiment is different from the endoscope system 100 according to the first embodiment in the functional configuration of the main body 8 and the like.

Figure 8:
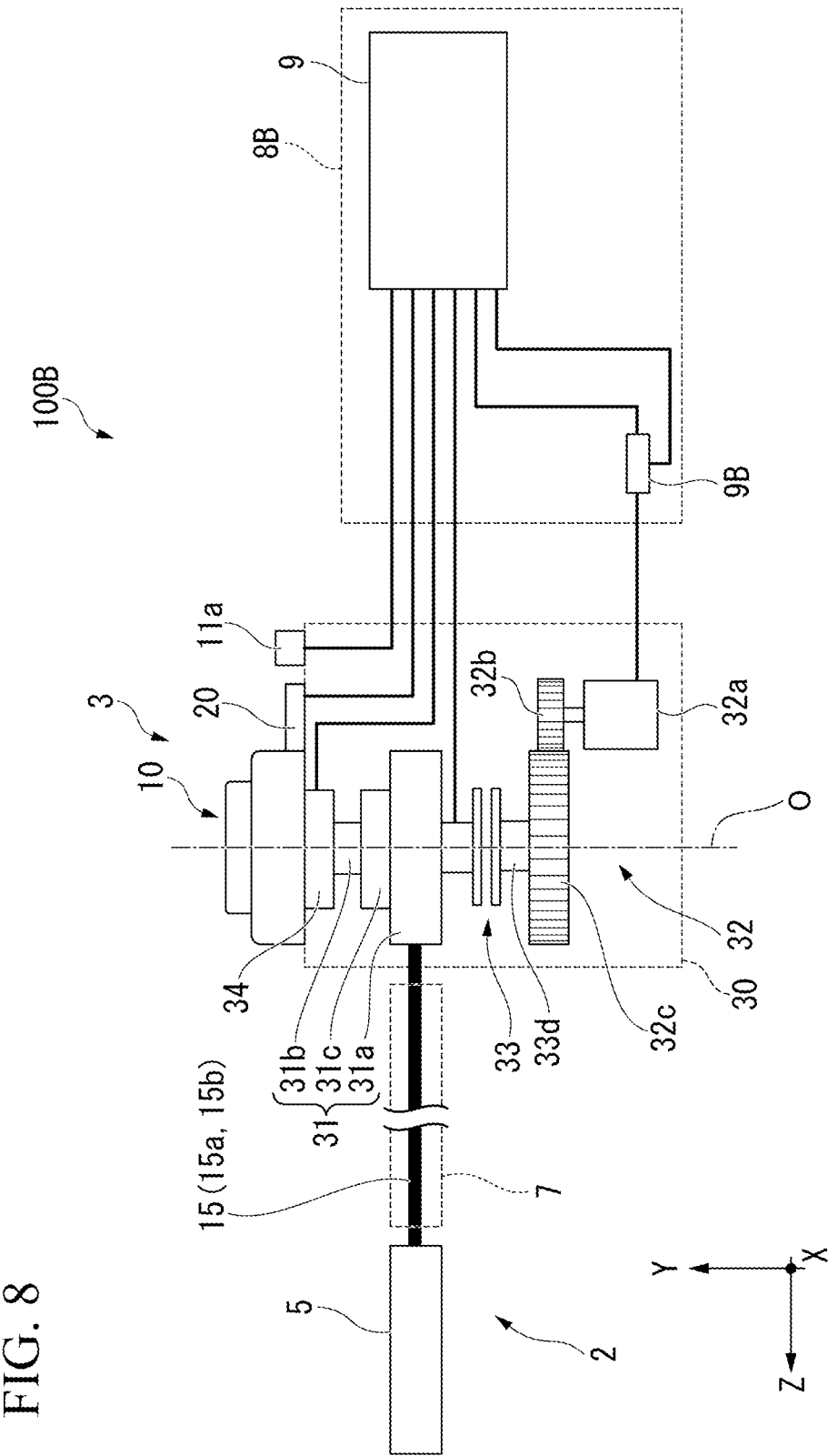
FIG. 8 is a schematic diagram showing an insertion portion, an operation portion, and a controller of an endoscope system according to a second embodiment of the present disclosure.

FIG. 8 is a schematic view showing the insertion portion 2, the operation portion 3, and a main body 8B of the endoscope system 100B.

The endoscope system 100B has the insertion portion 2, the operation portion 3, the universal cable 4, and the main body 8B.

The main body 8B has the control portion 9 and a current sensor 9B. The current sensor 9B is configured to determine the current flowing to the motor 32a so as to determine the rotation torque as the output of the motor 32a according to the current.

Operations of the endoscope system 100B having the above-described configuration will be described by referring to the flow chart shown in FIG. 9.

[Operation of Switching the Electrical Operation Mode to Manual Operation Mode]

FIG. 9 is a flow chart regarding the control processing of the control portion 9 when the operation mode is switched from the electrical operation mode to the manual operation mode. As shown in FIG. 9, when the operation mode of the control portion 9 is switched to the electrical operation mode, the control portion 9 starts the control processing of the electrical operation mode (Step S30). The control portion 9 subsequently executes Step S31.

During Step S31, in the case in which the operation mode is not the electrical operation mode, the control portion 9 controls the clutch mechanism 33 to connect the first shaft member 31b and the second shaft member 32d (engage the clutch). The control portion 9 drives the motor 32a of the electrical driving portion 32 so as to control the bending portion 6 by the electrical operation. After a predetermined period, the control portion 9 subsequently executes Step S32.

During Step S32, the control portion 9 detects whether there is a pressing operation to the operation-mode-switching button 11a. In the case in which it is detected that the operation-mode-switching button 11a is pressed, the operator intends to change the operation mode from the electrical operation mode to the manual operation mode. In this case, the control portion subsequently executes Step S33. On the other hand, in the case in which it is not detected that the operation-mode-switching button 11a is pressed, the control portion 9 executes Step S31 again.

During Step S33, the control portion 9 obtains the rotation angle of the pulley 31a and the operation knob 10 from the potentiometer 31c. The control portion 9 may accurately obtain the rotation angle of the pulley 31a and the operation knob 10 due to the electrical operation. The control portion 9 subsequently executes Step S34.

During Step S34, the control portion 9 determines whether the rotation angle of the operation knob 10 detected during Step S33 is equal to or larger than the predetermined amount (for example, 90 degrees). In the case in which the rotation angle is equal to or larger than the predetermined amount, the control portion 9 subsequently executes Step S35. In the case in which the rotation angle is not equal to or larger than the predetermined amount, even if the clutch of the clutch mechanism 33 is disengaged to cancel the transmission of the second force, the control portion 9 determines that the bending portion 6 does not rapidly operate to enter the straight stage immediately after the disengagement of the clutch. In this case, the control portion subsequently executes Step S36 to switch the operation mode to the manual operation mode.

During Step S35, the control portion 9 determines the rotation torque as the output of the motor 32a. The control portion 9 controls the current flowing to the motor 32a to be smaller so as to make the determined rotation torque to be smaller. The force (second force) for rotating the pulley 31a by the electrical driving portion 32 becomes smaller such that the rotation angle of the pulley 31a becomes smaller and the pulley 31a approaches the initial state. The control portion 9 subsequently executes Step S33 again.

The control portion 9 repeats Step S33 to Step S35 such that the rotation angle of the operation knob 10 gradually becomes smaller and the pulley 31 gradually approaches the initial state. As a result, the control processing of the control portion 9 is branched to Step S36 at Step S34 to switch the operation mode to the manual operation mode.

According to the endoscope system 100B disclosed in the present embodiment, it is possible to prevent the bending portion 6 from rapidly operating to enter the straight state by switching the operation mode from the electrical operation mode to the manual operation mode. The endoscope system 100B may be transitioned to the manual operation mode after gradually returning the bending portion in the bent state to the straight state.

The first embodiment of the present disclosure has been described above in details; however, the specific configuration is not limited to the embodiment, and additions, omissions, substitutions and other changes in the structure are possible without departing from the spirit of the present disclosure. The configuration elements shown in the first embodiment and following modification examples may be suitably combined.

Several embodiments and modification examples of the present disclosure have been described above, however, technical scope of the present disclosure is not limited to the embodiment and the application examples. The present disclosure is not limited to the above-described embodiments and is limited only by the accompanying claims.

What is claimed is:

1. A manipulator system, comprising:
   an elongated portion having a bending portion and a wire configured to bend the bending portion;
   an operation portion configured to generate a first force for pulling the wire by an operator;
   a motor configured to generate a second force for pulling the wire;
   a clutch mechanism configured to switch a pulling force to pull the wire to at least one of the first force or the second force;
   one or more sensors mounted on the operation portion, the one or more sensors being configured to determine a grasping state of the operation portion by the operator; and
   a controller comprising hardware, the controller being configured to control the motor and the clutch mechanism,
   wherein the controller is further configured to:
      obtain the grasping state from the one or more sensors,
      generate a control signal for controlling the clutch mechanism according to the obtained grasping state, and
      transmit the control signal to the clutch mechanism,
   wherein the controller is configured to have a manual operation mode in which only the first force is utilized as the pulling force and an electrical operation mode in which only the second force is utilized as the pulling force, and
   wherein the manual operation mode and the electrical operation mode are switched according to the control signal from the controller.

2. The manipulator system according to claim 1, wherein when the control signal is generated for switching the operation mode from the manual operation mode to the electrical operation mode, the controller is configured to switch the pulling force from the first force to the second force such that a ratio of the first force with respect to the pulling force is gradually decreased while a ratio of the second force with respect to the pulling force is gradually increased with time, and
   wherein when the control signal is generated for switching the operation mode from the electrical operation mode to the manual operation mode, the controller is configured to switch the pulling force from the second force to the first force such that a ratio of the second force with respect to the pulling force is gradually decreased while a ratio of the first force with respect to the pulling force is gradually increased with time.

3. The manipulator system according to claim 1, wherein when the controller receives an instruction to switch the operation mode from the electrical operation mode to the manual operation mode and in a case in which the second force is less than a predetermined amount, the controller is configured to switch the electrical operation mode to the manual operation mode in despite of the grasping state.

4. The manipulator system according claim 1, wherein when the controller receives an instruction to switch the operation mode from the electrical operation mode to the manual operation mode and in a case in which the first force determined from the input to the operation portion is equivalent to the second force, the controller is configured to switch the electrical operation mode to the manual operation mode.

5. The manipulator system according to claim 4, wherein in a case in which the first force determined from the grasping state is not equivalent to the second force and the wire is unmovably fixed, the controller is configured to switch the electrical operation mode to the manual operation mode.

6. The manipulator system according to claim 1, wherein when the controller is operated in the manual operation mode, in a case in which an external force applied to the operation portion that is detected from the grasping state is less than a predetermined amount and the bending portion is bent at an angle larger than a predetermined angle, the controller is configured to switch the operation mode to the electrical operation mode.

7. The manipulator system according to claim 1, further comprises a pulley configured to pull the wire,
   wherein the operation portion has an operation knob configured to rotate the pulley, and
   wherein in the electrical operation mode, the operation knob is rotated together with the pulley due to the second force.

8. The manipulator system according to claim 7, wherein when the controller receives the instruction to switch from the electrical operation mode to the manual operation mode, in a case in which a rotation angle of the operation knob is smaller than a predetermined amount, the controller is configured to switch the electrical operation mode to the manual operation mode in despite of the grasping state.

9. The manipulator system according to claim 7, wherein when the controller receives the instruction to switch from the electrical operation mode to the manual operation mode, in a case in which a rotation torque applied to the operation knob is equivalent to a rotation angle of the operation knob, the controller is configured to switch from the electrical operation mode to the manual operation mode.

10. The manipulator system according to claim 9, wherein in a case in which the rotation torque applied to the operation knob is not equivalent to the rotation angle of the operation knob and the wire is unmovably fixed, the controller is configured to switch the electrical operation mode to the manual operation mode.

11. The manipulator system according to claim 7, wherein when the controller is operated in the manual operation mode, in a case in which the external force applied to the operation knob that is determined from the grasping state is less than a predetermined amount and the rotation angle of the operation knob is larger than the predetermined angle, the controller is configured to switch to the electrical operation mode.

* * * * *